(12) United States Patent
Horiuchi et al.

(10) Patent No.: US 12,426,847 B2
(45) Date of Patent: Sep. 30, 2025

(54) IMAGING APPARATUS, IMAGING SYSTEM, CONTROL METHOD, AND CONTROL PROGRAM

(71) Applicant: FUJIFILM Corporation, Tokyo (JP)

(72) Inventors: Hisatsugu Horiuchi, Kanagawa (JP); Atsushi Osawa, Kanagawa (JP); Lisako Nobuyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1 day.

(21) Appl. No.: 18/592,448

(22) Filed: Feb. 29, 2024

(65) Prior Publication Data
US 2024/0298996 A1    Sep. 12, 2024

(30) Foreign Application Priority Data

Mar. 10, 2023 (JP) .................... 2023-038157

(51) Int. Cl.
*A61B 6/00* (2024.01)
*A61B 6/04* (2006.01)
*A61B 6/50* (2024.01)
*A61B 8/00* (2006.01)
*A61B 8/08* (2006.01)
*A61B 90/00* (2016.01)

(52) U.S. Cl.
CPC ............ *A61B 6/547* (2013.01); *A61B 6/0414* (2013.01); *A61B 6/502* (2013.01); *A61B 8/0825* (2013.01); *A61B 8/403* (2013.01); *A61B 8/5261* (2013.01); *A61B 2090/3925* (2016.02)

(58) Field of Classification Search
CPC ....... A61B 6/547; A61B 6/0414; A61B 6/502; A61B 8/0825; A61B 8/40–406; A61B 8/5261; A61B 2090/3925
See application file for complete search history.

(56) References Cited

U.S. PATENT DOCUMENTS

| | | | |
|---|---|---|---|
| 2003/0181801 A1* | 9/2003 | Lasser | A61B 6/4417 600/407 |
| 2004/0039285 A1* | 2/2004 | Ustuner | A61B 8/587 600/459 |
| 2012/0059247 A1* | 3/2012 | Speeg | A61B 10/0275 600/567 |
| 2020/0305835 A1* | 10/2020 | Arai | A61B 8/4416 |
| 2020/0305836 A1* | 10/2020 | Arai | A61B 8/4416 |
| 2020/0375562 A1 | 12/2020 | Arai et al. | |

FOREIGN PATENT DOCUMENTS

| | | |
|---|---|---|
| JP | 2006280444 A | 10/2006 |
| JP | 2020192181 A | 12/2020 |

* cited by examiner

*Primary Examiner* — Sean D Mattson
(74) *Attorney, Agent, or Firm* — Studebaker Brackett PLLC (57) ABSTRACT

An imaging apparatus including: an imaging table having an imaging surface on which at least one marker is disposed; a compression member for putting a breast disposed on the imaging surface into a compressed state; and an ultrasound probe that obtains an ultrasound image of the breast put into the compressed state by the compression member.

8 Claims, 9 Drawing Sheets

IMAGING APPARATUS, IMAGING SYSTEM, CONTROL METHOD, AND CONTROL PROGRAM

CROSS-REFERENCE TO RELATED APPLICATIONS

This application claims priority from Japanese Application No. 2023-038157, filed on Mar. 10, 2023, the entire disclosure of which is incorporated herein by reference.

BACKGROUND

Technical Field

The present disclosure relates to an imaging apparatus, an imaging system, a control method, and a control program.

Related Art

In the related art, a mammography apparatus that captures a radiation image of a breast is known. In addition, in the terms of improving the detection accuracy of a specific type of a lesion and improving the efficiency of an examination, an apparatus that can capture an ultrasound image of a breast in addition to a radiation image is proposed. For example, JP2020-192181A discloses that a radiation image of a breast in a compressed state is captured and then an ultrasound image of the breast is continuously captured in a state of maintaining the compressed state. In addition, for example, JP2006-280444A discloses a method of using an X-ray apparatus, an MR apparatus, and a treatment apparatus to easily specify the same lesion position among the X-ray apparatus, the MR apparatus, and the treatment apparatus while the breast is compressed. JP2006-280444A describes that an image marker for position registration is provided in a compression plate, a bed, a chair, a patient, or the like in order to specify the lesion position.

By the way, in the ultrasound image, according to the principle of irradiating an object with ultrasound and receiving the reflected waves, the image is less clear as a distance from an irradiation unit is increased. Therefore, as described in JP2020-192181A, in a case in which the breast put into the compressed state between the imaging table and a compression member is irradiated with the ultrasound from above the compression member, the ultrasound image is less clear as a distance from the compression member side is increased and a distance from the imaging table side is decreased. Theoretically, in a case of ultrasound measurement, the distance from the irradiation unit and a resolution can be approximately calculated. However, there are individual differences in a size of the breast and a composition of the breast (for example, a ratio and a distribution of a fat tissue and a mammary gland tissue), and there is a possibility that the calculated resolution remains at about a reference value. Then, there is a need for a technique that can check whether or not the ultrasound image with sufficient accuracy can be captured in the breast of an examination target, particularly in a portion away from the irradiation unit of the ultrasound.

SUMMARY

The present disclosure provides an imaging apparatus, an imaging system, a control method, and a control program that can support capturing of an ultrasound image with the accuracy that enables to read a marker provided on an imaging table.

A first aspect of the present disclosure relates to an imaging apparatus comprising: an imaging table having an imaging surface on which at least one marker is disposed; a compression member for putting a breast disposed on the imaging surface into a compressed state; and an ultrasound probe that obtains an ultrasound image of the breast put into the compressed state by the compression member.

In the first aspect, the marker may be formed of a material having a different acoustic impedance from at least a region adjacent to the marker on the imaging surface.

In the first aspect, the marker may be a portion formed in a recess shape or a protrusion shape with respect to the imaging surface.

In the first aspect, three or more markers having different intervals between adjacent markers may be disposed on the imaging surface.

In the first aspect, the imaging apparatus may further comprise a radiation source that irradiates the breast put into the compressed state by the compression member with radiation, in which the marker is disposed on the imaging surface in a region other than an irradiation field of the radiation.

A second aspect of the present disclosure relates to an imaging system comprising: the imaging apparatus according to the first aspect; and a control apparatus including at least one processor, in which the processor acquires the ultrasound image of the breast obtained by the ultrasound probe, detects the marker from the ultrasound image, and gives a warning in a case in which the marker is not detectable from the ultrasound image.

In the second aspect, the processor may acquire a tomographic image on each of a plurality of tomographic planes of the breast put into the compressed state by the compression member, may specify a depth position in a compression direction from a contact surface between the compression member and the breast for a region of interest included in the breast based on a plurality of the tomographic images, and may give a warning in a case in which the depth position of the region of interest is equal to or greater than a predetermined threshold value and the marker is not detectable from the ultrasound image.

A third aspect of the present disclosure relates to a control method comprising: acquiring an ultrasound image of a breast that is disposed on an imaging surface, on which at least one marker is disposed, of an imaging table having the imaging surface, and is put into a compressed state by a compression member; detecting the marker from the ultrasound image; and giving a warning in a case in which the marker is not detectable from the ultrasound image.

A fourth aspect of the present disclosure relates to a control program for causing a computer to execute a process comprising: acquiring an ultrasound image of a breast that is disposed on an imaging surface, on which at least one marker is disposed, of an imaging table having the imaging surface, and is put into a compressed state by a compression member; detecting the marker from the ultrasound image; and giving a warning in a case in which the marker is not detectable from the ultrasound image.

According to the aspects described above, the imaging apparatus, the imaging system, the control method, and the control program according to the present disclosure can support capturing of the ultrasound image with the accuracy that enables to read the marker provided on the imaging table.

DETAILED DESCRIPTION

Hereinafter, a description of an embodiment of the present disclosure will be made with reference to the accompanying drawings.

Figure 1:
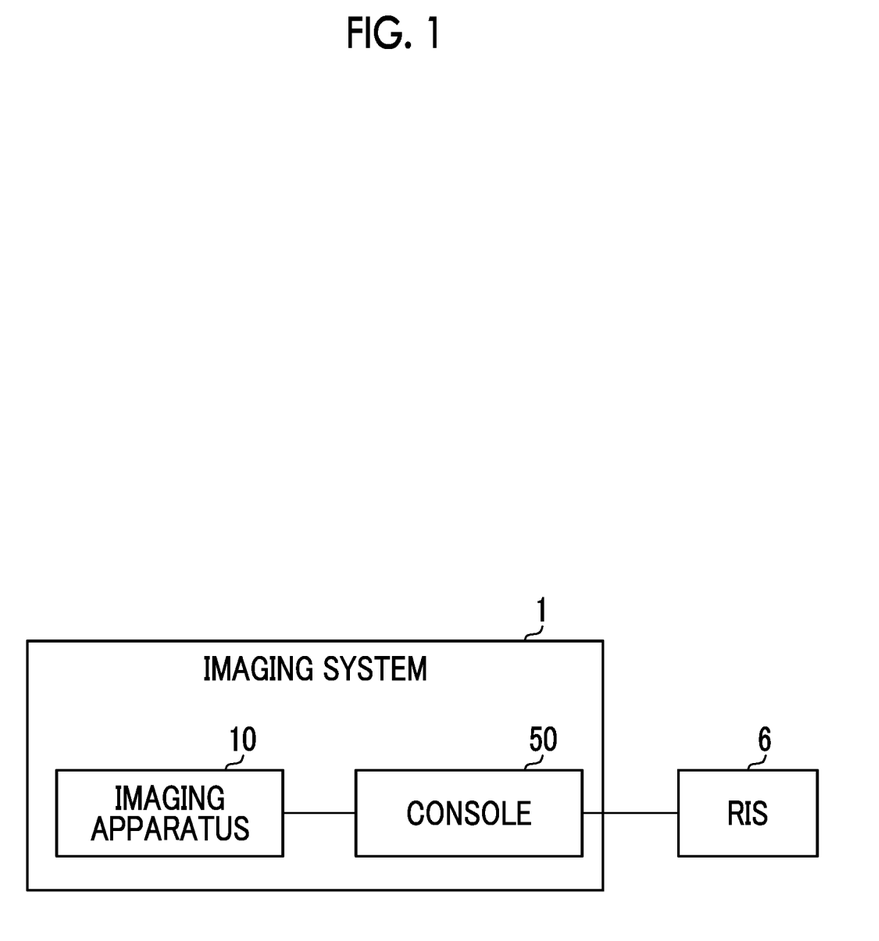
FIG. 1 is a view showing an example of a schematic configuration of an imaging system.

First, a description of a configuration of an imaging system 1 will be made with reference to FIG. 1. FIG. 1 is a view showing an example of a schematic configuration of the imaging system 1. As shown in FIG. 1, the imaging system 1 comprises an imaging apparatus 10 and a console 50. The imaging apparatus 10 and the console 50, and the console 50 and an external radiology information system (RIS) 6 are configured to be connected to each other via a wired or wireless network.

In the imaging system 1, the console 50 acquires an imaging order or the like from the RIS 6, and controls the imaging apparatus 10 in accordance with the imaging order, an instruction from the user, and the like. The imaging apparatus 10 acquires a radiation image and an ultrasound image of a breast of an examinee put into a compressed state by a compression member 40 as a subject. The console 50 is an example of a control apparatus according to the present disclosure.

Figure 2:
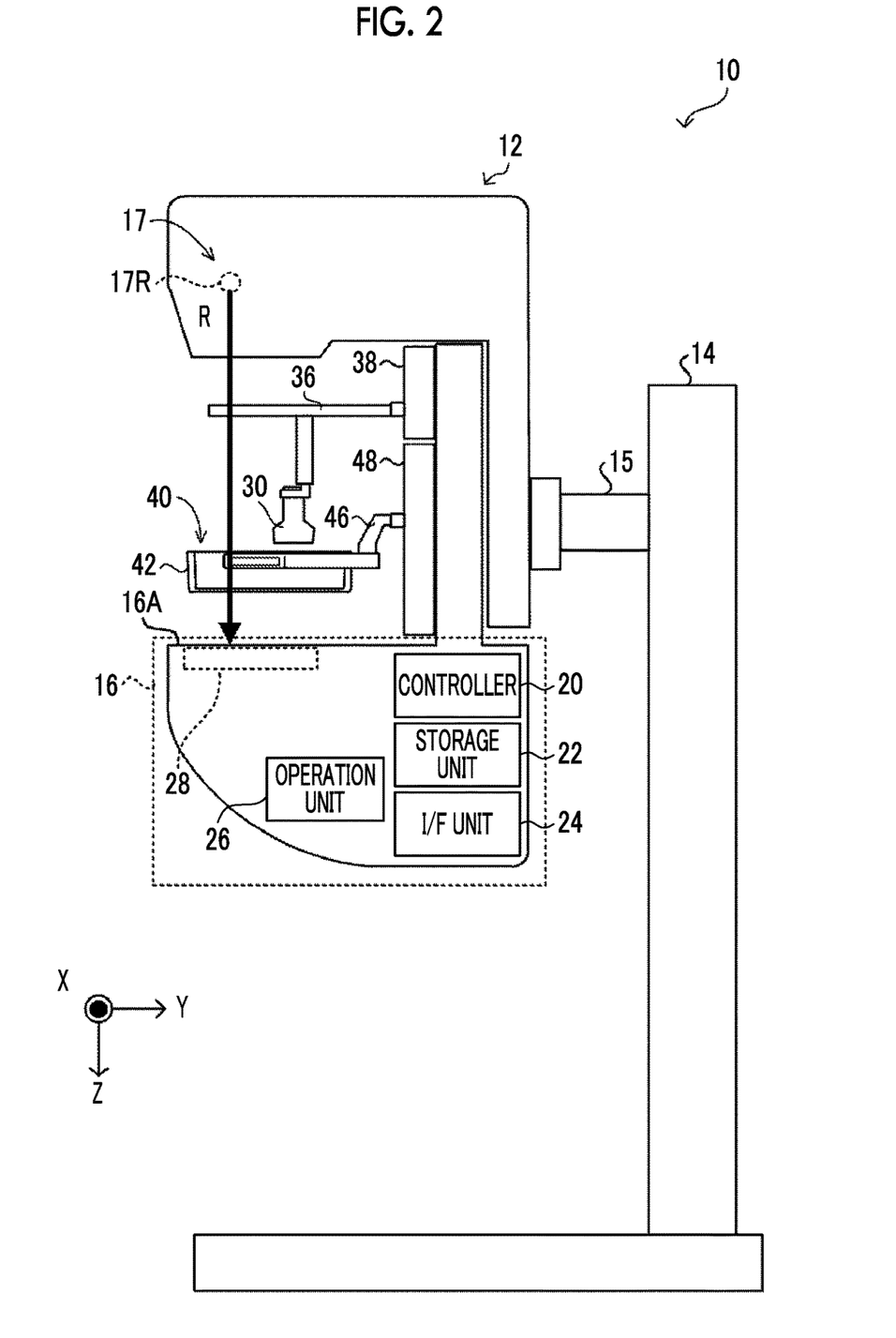
FIG. 2 is a side view showing an example of an appearance of an imaging apparatus.

Next, a description of a schematic configuration of the imaging apparatus 10 will be made with reference to FIG. 2. FIG. 2 is a side view showing an example of an appearance of the imaging apparatus 10, and is a view in a case in which the imaging apparatus 10 is viewed from a right side of the examinee. As shown in FIG. 2, the imaging apparatus 10 comprises a radiation source 17R, a radiation detector 28, an imaging table 16 disposed between the radiation source 17R and the radiation detector 28, the compression member 40 that compresses the breast between the compression member 40 and the imaging table 16, and an ultrasound probe 30 disposed between the radiation source 17R and the compression member 40. In the imaging apparatus 10, a user, such as a doctor or a technician, positions the breast of the examinee on an imaging surface 16A of the imaging table 16.

The imaging apparatus 10 comprises an arm part 12, a base 14, and a shaft part 15. The arm part 12 is held to be movable in an up-down direction (Z direction) by the base 14. The shaft part 15 connects the arm part 12 to the base 14. The arm part 12 is relatively rotatable with respect to the base 14 with the shaft part 15 as a rotation axis. In addition, the arm part 12 may be relatively rotatable with respect to the base 14 with the shaft part 15 as the rotation axis separately between an upper part comprising a radiation emitting unit 17 and a lower part comprising the imaging table 16.

The arm part 12 comprises the radiation emitting unit 17 and the imaging table 16. The radiation emitting unit 17 comprises the radiation source 17R, and is configured to change an irradiation field of radiation (for example, X-rays) emitted from the radiation source 17R. For example, the change of the irradiation field may be performed by the user operating an operation unit 26, or may be performed by a controller 20 in accordance with a type of the attached compression member 40. The radiation source 17R irradiates the breast put into the compressed state by the compression member 40 with radiation R.

The imaging table 16 comprises the controller 20, a storage unit 22, an interface (I/F) unit 24, the operation unit 26, and the radiation detector 28. The controller 20 controls an overall operation of the imaging apparatus 10 in accordance with the control of the console 50. The controller 20 comprises a central processing unit (CPU), a read only memory (ROM), a random access memory (RAM), and the like (none shown). The ROM stores in advance various programs including a program executed by the CPU for performing the control related to the acquisition of the radiation image and the ultrasound image. The RAM transitorily stores various data.

Data of the radiation image and the ultrasound image, various types of other information, and the like are stored in the storage unit 22. The storage unit 22 is realized by, for example, a storage medium, such as a hard disk drive (HDD), a solid state drive (SSD), and a flash memory.

The I/F unit 24 performs communication of various types of information with the console 50 by wired or wireless communication. Specifically, the I/F unit 24 receives information related to the control of the imaging apparatus 10 from the console 50. Further, the I/F unit 24 transmits the data of the radiation image and the ultrasound image to the console 50.

The operation unit 26 is a part that is provided on the imaging table 16 or the like and can be operated by the user with a hand, a foot, or the like, and is, for example, a switch, a button, or a touch panel. For example, the operation unit 26 may receive a voice input from the user.

The radiation detector 28 is disposed in the imaging table 16, detects the radiation R transmitted through the breast and the imaging table 16, generates the radiation image based on the detected radiation R, and outputs image data indicating the generated radiation image. It should be noted that a type of the radiation detector 28 is not particularly limited and may be, for example, an indirect conversion type radiation detector that converts the radiation R into light and converts the converted light into a charge, or a direct conversion type radiation detector that directly converts the radiation R into a charge.

A probe unit 38 and a compression unit 48 are connected to the arm part 12. A support part 36 that attachably and detachably supports the ultrasound probe 30 is attached to the probe unit 38. The support part 36 (ultrasound probe 30) is moved in the up-down direction (Z direction) and a horizontal direction (X direction and Y direction) by a driving unit (not shown) provided in the probe unit 38. It is preferable that the support part 36 is formed of a material that transmits the radiation R.

The ultrasound probe 30 is used to obtain the ultrasound image of the breast put into the compressed state by the compression member 40, is disposed between the radiation source 17R and the compression member 40, irradiates the breast with ultrasound via the compression member 40, and receives the reflected waves from the breast. Specifically, the ultrasound probe 30 comprises an ultrasound transducer array. The ultrasound transducer array is configured such that a plurality of ultrasound transducers are arranged one-dimensionally or two-dimensionally. The ultrasound transducer is formed, for example, such that electrodes are formed on both ends of a piezoelectric body, such as a piezoelectric ceramic represented by lead (Pb) zirconate titanate (PZT) or a polymer piezoelectric element represented by polyvinylidene difluoride (PVDF). The probe unit 38 includes a converter (not shown) that converts the reflected waves from the breast received by the ultrasound probe 30 into the ultrasound image, and the ultrasound image is obtained by the converter.

In addition, a plurality of types of the ultrasound probes 30 different from each other may be attachable to the imaging apparatus 10. For example, depending on a physique of the examinee (for example, a size of the breast), a tissue composition of the breast (for example, a fat mass and a mammary gland mass), a type of imaging (for example, magnification imaging and spot imaging), and the like, the ultrasound probes 30 having different types from each other may be prepared and can be attached to and detached from the imaging apparatus 10. For example, the ultrasound probes 30 having different performances and dimensions from each other may be selectively used, such as a linear probe having a center frequency of about 7.5 MHz (for superficial use or the like), a convex probe having a center frequency of about 3.5 MHz (for abdomen or the like), and a sector probe having a center frequency of about 2.5 MHz (for heart or the like).

A support part 46 that supports the compression member 40 is attachably and detachably attached to the compression unit 48. The support part 46 (compression member 40) is moved in the up-down direction (Z direction) by a driving unit (not shown) provided in the compression unit 48.

Figure 3:
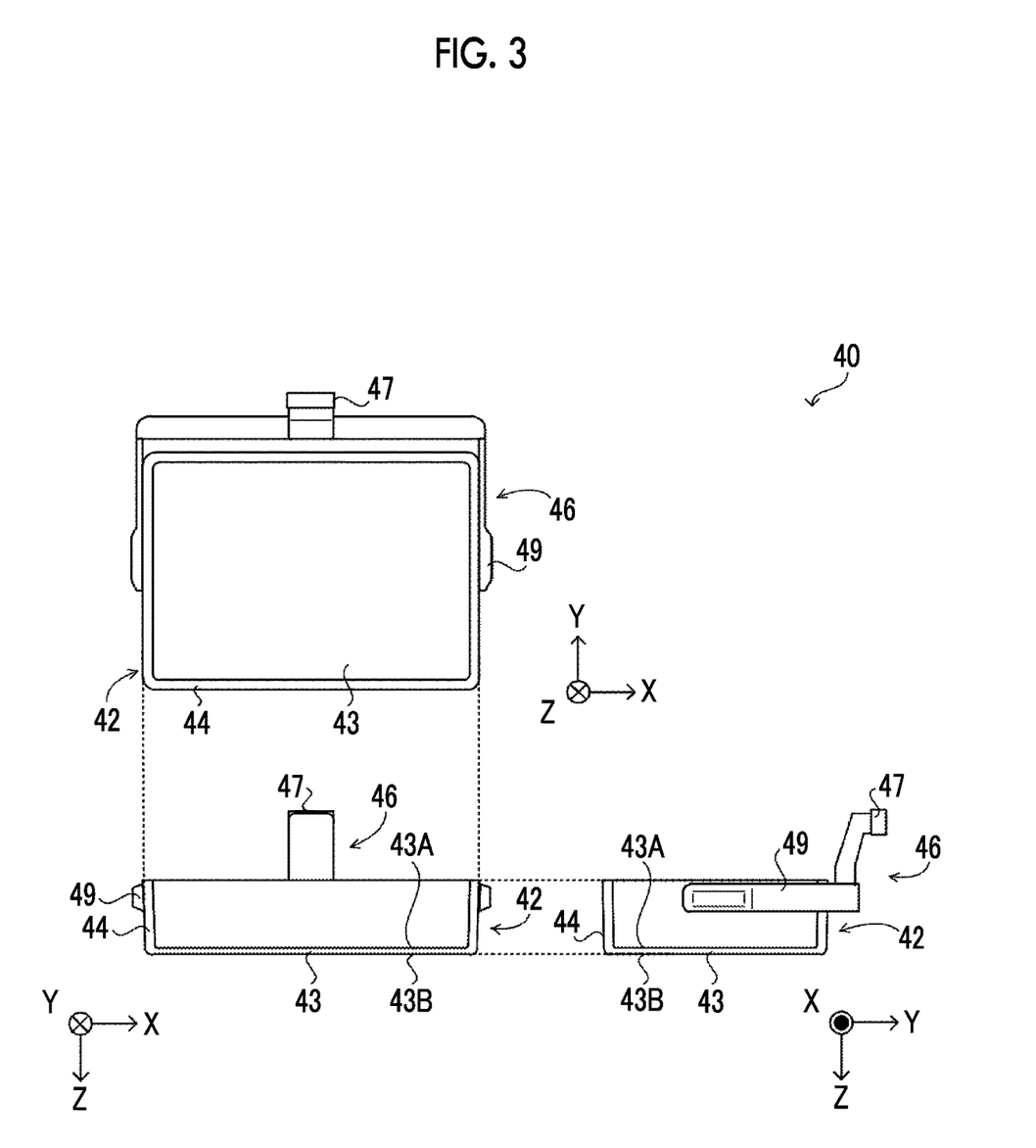
FIG. 3 is a three-orthographic view showing an example of a schematic configuration of a compression member.

The compression member 40 is used to put the breast disposed on the imaging surface 16A into the compressed state. Specifically, the compression member 40 is disposed between the radiation source 17R and the imaging table 16 and interposes the breast between the compression member 40 and the imaging table 16 to put the breast into the compressed state. FIG. 3 shows a three-orthographic view of an example of the compression member 40. The three-orthographic view of FIG. 3 includes a top view of the compression member 40 as viewed from above (radiation emitting unit 17 side), a side view thereof as viewed from the examinee side, and a side view thereof as viewed from the right side of the examinee. As shown in FIG. 3, the compression member 40 includes a compression part 42 and the support part 46.

The support part 46 includes an attachment part 47 and an arm 49. The attachment part 47 attaches the compression member 40 to the imaging apparatus 10, specifically, the driving unit of the compression unit 48. The arm 49 supports the compression part 42.

The compression part 42 includes a bottom part 43 formed to be substantially flat and surrounded by a wall part 44 having a substantially uniform height, and has a cross section shape formed in a recess shape. It is preferable that the compression part 42 is formed of an optically transparent or translucent material in order to perform positioning and check of the compressed state in the compression of the breast. In addition, it is preferable that the compression part 42 is formed of a material excellent in a transmittance of the radiation R and the ultrasound. In addition, it is preferable that the compression part 42 is formed of, for example, a material excellent in strength, such as drop strength and compression strength.

As such a material, for example, resin, such as polymethylpentene (PMP), polycarbonate (PC), acryl, polypropylene (PP), and polyethylene terephthalate (PET), can be used. In particular, in the polymethylpentene, an acoustic impedance, which affects the transmittance and the reflectivity of the ultrasound, is closer to an acoustic impedance of a human body (breast) than other materials, and a proportion of the noise on the ultrasound image can be decreased. Therefore, as the material of the compression part 42, the polymethylpentene is suitable.

In addition, a plurality of types of the compression members 40 different from each other may be attachable to the imaging apparatus 10. For example, depending on a physique of the examinee (for example, a size of the breast), a tissue composition of the breast (for example, a fat mass and a mammary gland mass), a type of imaging (for example, magnification imaging and spot imaging), and the like, compression members 40 having different types from each other may be prepared and can be attached to and detached from the imaging apparatus 10. Specifically, a compression member in accordance with the size of the breast, a compression member for axilla imaging, a compression member for magnification imaging, and a compression member for so-called spot imaging that captures the radiation image of only a region in which a lesion exists, and the like may be used. That is, the compression member 40 is not limited to the compression member that compresses the entire breast, and may have a smaller size than the breast to compress a part of the breast.

Figure 4:
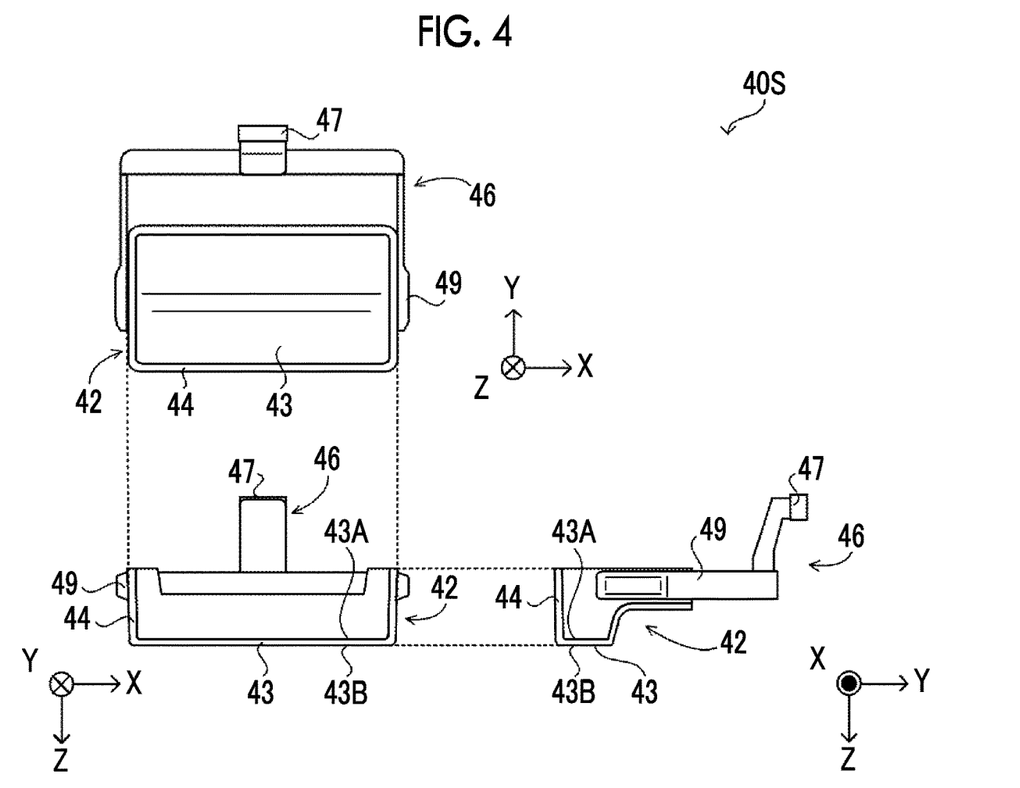
FIG. 4 is a three-orthographic view showing an example of the schematic configuration of the compression member.

FIG. 4 shows a three-orthographic view of a compression member 40S for a small breast as an example of another form different from the compression member 40 of FIG. 3. The three-orthographic view of FIG. 4 includes a top view of the compression member 40S as viewed from above (radiation emitting unit 17 side), a side view thereof as viewed from the examinee side, and a side view thereof as viewed from the right side of the examinee. The compression member 40S includes the compression part 42 and the support part 46, as in the compression member 40 in FIG. 3. In the compression member 40S, the bottom part 43 is not flat, and the attachment part 47 side is higher than a chest wall side (side away from the attachment part 47). In addition, the height of the wall part 44 is not uniform, and a height of a part of the chest wall side is lower than a height of other parts. Due to such a shape, the compression member 40S can easily perform the positioning and the compression even for the small breast.

As described above, in the imaging apparatus 10, at least one of the compression member 40 for putting the breast into the compressed state or the ultrasound probe 30 for acquiring the ultrasound image may be attachable and detachable. That is, a plurality of types of the compression members 40 and the ultrasound probes 30 having different dimensions from each other may be attachable to the imaging apparatus 10. In this case, the imaging apparatus 10 may detect the types of the compression member 40 and the ultrasound probe 30 that are attached.

For example, the attachment part 47 of the compression member 40 may be provided with a plurality of pins having different dispositions for each type of the compression member 40 as identification information, and the identification information may be read by a sensor (for example, a photointerrupter) that can detect the disposition of the pins provided in the compression unit 48. In addition, for example, a marker (for example, a bar code and a two-dimensional code) in accordance with the type of the compression member 40 may be provided at any position of the compression member 40 as identification information, and the identification information may be read by a sensor (for example, a charge coupled device (CCD) sensor) that can detect the marker.

In addition, for example, a radio frequency identification (RFID) tag having identification information in accordance with the type of the compression member 40 may be provided at any position of the compression member 40, and the identification information may be read by an RFID reader that can read the RFID tag. In addition, for example, a weight of each type of the compression member 40 and identification information may be stored in the storage unit 22 in advance in association with each other, the weight of the attached compression member 40 may be measured by a sensor that can detect the weight, and the identification information (type of the compression member 40) may be specified based on a measured value.

Similarly, for the ultrasound probe 30, the type of the attached ultrasound probe 30 may be identified in accordance with, for example, the pin, the marker, the RFID tag, or the weight.

It should be noted that a gel-like or liquid medium having an ultrasound transmittance may be applied to an upper surface 43A of the bottom part 43 of the compression member 40 and/or a contact surface 43B with the breast. As such a medium, for example, a known jelly for an ultrasound examination, which has the acoustic impedance close to the acoustic impedance of the human body (breast), can be applied. That is, the imaging apparatus 10 may acquire the ultrasound image of the breast put into the compressed state by the compression member 40 in a state of being coated with the gel-like or liquid medium having the ultrasound transmittance, via the compression member 40. In this case, it is possible to suppress entry of air into an interface between an ultrasound radiation surface of the ultrasound probe 30 and the upper surface 43A and/or an interface between the contact surface 43B and the breast, and it is possible to reduce a difference in the acoustic impedance at each interface, so that the proportion of the noise applied to the ultrasound image can be decreased.

Figure 5:
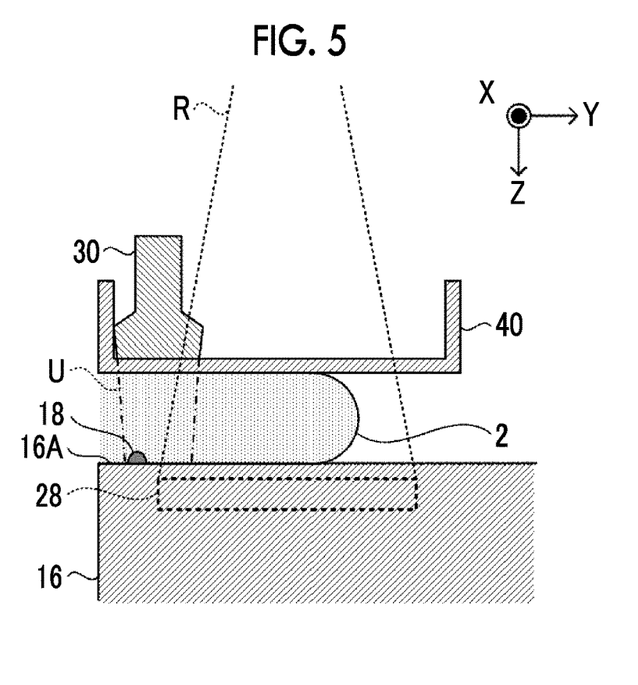
FIG. 5 is a view showing an example of a schematic configuration of a marker disposed on an imaging surface.
Figure 6:
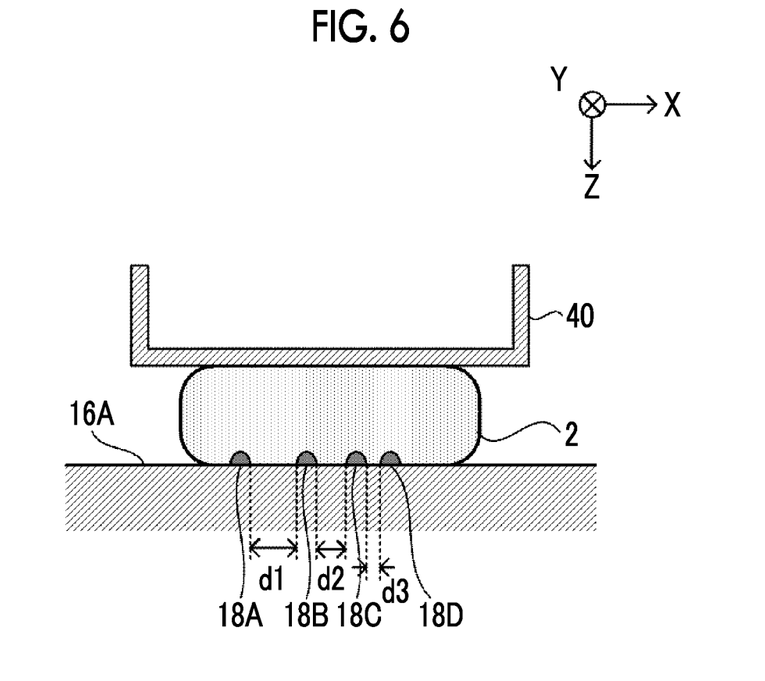
FIG. 6 is a view showing an example of the schematic configuration of the marker disposed on the imaging surface.

The imaging table 16 has the imaging surface 16A on which at least one marker 18 is disposed. FIGS. 5 and 6 show examples of a partially magnified view of the imaging surface 16A on which the marker 18 is disposed. FIG. 5 is a view showing a case in which the imaging apparatus 10 is viewed from the right side of the examinee. FIG. 6 is a view showing a case in which the imaging apparatus 10 is viewed from the chest wall side to a nipple side of the examinee. In FIGS. 5 and 6, some components that are not necessary for description will be omitted.

As described above, in the ultrasound image, according to the principle of irradiating the breast 2 with ultrasound U and receiving the reflected waves, the obtained image less clear as a distance from the ultrasound probe 30 is increased.

Then, the imaging apparatus 10 according to the present disclosure includes, on the imaging surface 16A, a marker 18 for checking whether or not the ultrasound image with sufficient accuracy can be captured in the breast 2 that is an examination target, particularly in a portion on the imaging surface 16A side away from the ultrasound probe 30. That is, in a case in which the marker 18 is included in the captured ultrasound image, it can be seen that the ultrasound image with sufficient accuracy up to the portion on the imaging surface 16A side can be captured.

It is desirable that the marker 18 can be read in the ultrasound image but has a small influence on the radiation image. Hereinafter, a description of a specific example of the marker 18 will be made.

For example, the marker 18 may have a different shape from at least a region adjacent to the marker 18 on the imaging surface 16A. For example, as shown in FIGS. 5 and 6, the marker 18 may be a portion that is formed in a protrusion shape with respect to the imaging surface 16A. On the other hand, for example, the marker 18 may be a portion that is formed in a recess shape with respect to the imaging surface 16A. That is, the marker 18 can be detected in the ultrasound image by making a depth of the marker 18 different from the surrounding region. In a case in which the marker 18 is formed of the same material with unevenness, this case is a specific example in which the influence on the radiation image is small.

In addition, for example, the marker 18 may be formed of a different material from at least the region adjacent to the marker 18 on the imaging surface 16A. Specifically, the different material is a material having a different acoustic impedance. That is, it is preferable that the marker 18 is formed of a material having a different acoustic impedance from at least the region adjacent to the marker 18 on the imaging surface 16A. For example, the marker 18 may be made of polycarbonate, and the surrounding region of the marker 18 on the imaging surface 16A may be made of polymethylpentene. By making the material (that is, acoustic impedance) of the marker 18 different from the material of the surrounding region, the marker 18 can be more easily detected in the ultrasound image.

More specifically, it is preferable that the material of the marker 18 has a large difference in acoustic attenuation coefficient (suitably, equal to or greater than 0.2) from the material forming the adjacent region in the imaging surface 16A and has a small difference in X-ray absorption coefficient (suitably, equal to or smaller than 0.1). Selecting this material makes it possible to obtain the marker 18 that can be read in the ultrasound image but has a small influence on the radiation image. Examples of a combination of such materials include a combination of polyamide 6 (PA6) and polycarbonate. In particular, a case in which the material of the marker 18 is a material in which the absolute value of the X-ray absorption coefficient is significantly small (suitably, equal to or smaller than 0.2) is suitable because the marker 18 that has a particularly small influence on the radiation image can be obtained.

In addition, it is preferable that the material of the marker 18 has a small number of atoms and has the acoustic impedance greater than the acoustic impedance of the human body. Specific examples of such a material include beryllium (Be), graphite, and aluminum, and Be is particularly suitable. In a case in which the material having a small number of atoms is selected, it is possible to obtain the marker 18 that has a small influence on the radiation image. In addition, the difference from the breast in the ultrasound image is easily seen by selecting the material having the acoustic impedance greater than the acoustic impedance of the human body. It should be noted that the acoustic impedance is about 1.46 MRayl in the human body, is about 30.1 MRayl in Be, is about 39.6 MRayl in graphite, and is about 17.2 MRayl in aluminum.

In addition, for example, the marker 18 may be formed by adding an additive to the material that forms the region adjacent to the marker 18 on the imaging surface 16A. Examples of the additive include fibers, such as carbon, glass, rockwool (mineral glass), and cellulose. In a case in which the additive is added, the density and the stiffness are changed, and the acoustic impedance is also changed. Therefore, the change can be captured in the ultrasound image. In addition, in a case in which the additive is added to the extent, the change in the X-ray transmittance remains small, so that the influence on the radiation image can be reduced.

It should be noted that, in a case in which the material of the marker 18 is different from the material forming the adjacent region as described above, the marker 18 does not have to have a different shape (such as the protrusion shape or the recess shape) from the surrounding region. For example, the marker 18 may be embedded in the imaging surface 16A to form a plane continuous with the imaging surface 16A, or may be a thin film-like marker disposed on the imaging surface 16A.

In addition, for example, it is preferable that the marker 18 is disposed on the imaging surface 16A in a region other than the irradiation field of the radiation R as shown in FIG. 5. With this configuration, the marker 18 is not imaged in the radiation image and it is not necessary to be aware of the influence of the marker 18 on the radiation image, so that it is possible to increase a degree of freedom in selecting the material.

In addition, for example, three or more markers having different intervals between adjacent markers may be disposed on the imaging surface 16A. For example, FIG. 6 shows an example in which four markers 18A to 18D having different intervals d1 to d3 between the adjacent markers are disposed on the imaging surface 16A. In a case in which the intervals d1 to d3 between the adjacent markers are made different from each other in this manner, it is possible to check the resolution of the ultrasound image in addition to checking whether or not the ultrasound image can be captured up to a sufficient depth. For example, in the ultrasound image, in a case in which the markers 18A and 18B can be detected as different markers, but the markers 18C and 18D are integrally detected (see FIG. 9), it can be seen that the resolution is equal to or smaller than d2 and equal to or greater than d3.

It should be noted that the method of imaging the breast via the imaging apparatus 10 is not particularly limited. For example, cranio-caudal (CC) imaging, medio-lateral oblique (MLO) imaging, the magnification imaging and the spot imaging for imaging a part of the breast, and the like may be performed. The CC imaging is a method of imaging the breast in the compressed state by interposing the breast between the imaging table 16 and the compression member 40 in the up-down direction (Z direction). The MLO imaging is a method of imaging the breast in the compressed state including an axilla portion by interposing the breast between the imaging table 16 and the compression member 40 in a tilted state in which a rotation angle of the arm part 12 with respect to the base 14 is equal to or greater than 45 degrees and smaller than 90 degrees.

In addition, for example, the imaging apparatus 10 may perform tomosynthesis imaging. In the tomosynthesis imaging, the radiation R is emitted from each of a plurality of irradiation positions having different irradiation angles toward the breast by the radiation source 17R, to capture a plurality of radiation images of the breast. That is, in the tomosynthesis imaging, the imaging is performed by changing the rotation angle of the radiation emitting unit 17 with respect to the base 14 while fixing the angles of the imaging table 16, the compression member 40, the breast, and the like.

In addition, in the imaging apparatus 10, the breast of the examinee may be positioned not only in a state in which the examinee is standing (standing state) but also in a state in which the examinee is sitting on a chair, a wheelchair, or the like (sitting state).

The console 50 has a function of controlling the imaging apparatus 10 to acquire the radiation image in accordance with the imaging order acquired from the RIS 6, the instruction from the user, and the like. The console 50 has a function of detecting the marker 18 from the ultrasound image of the breast obtained by the ultrasound probe 30 and giving a warning in a case in which the marker 18 cannot be detected. Hereinafter, a description of the console 50 will be made.

Figure 7:
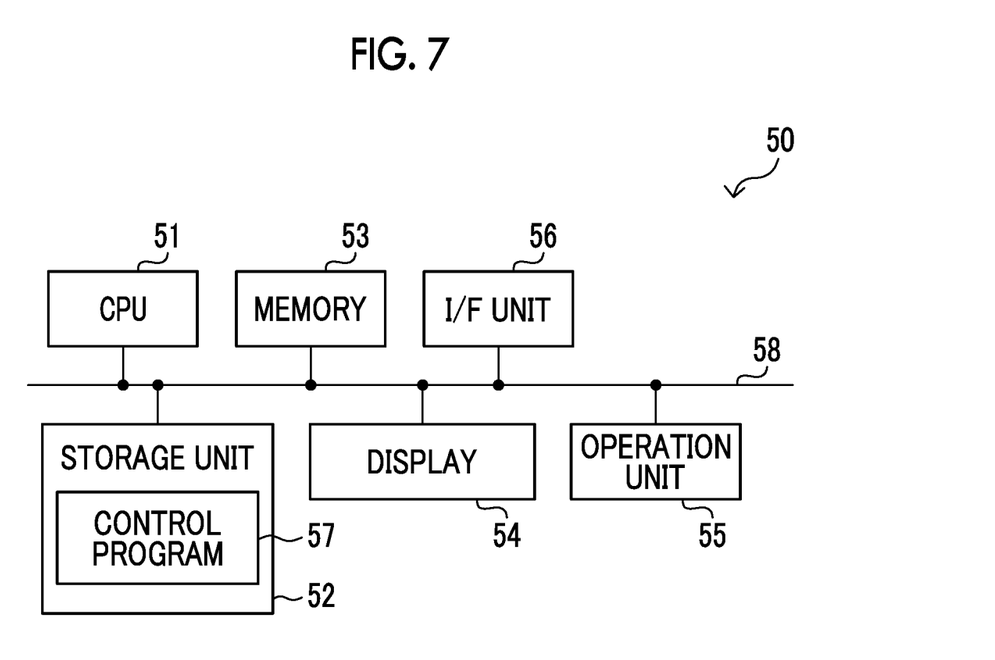
FIG. 7 is a block diagram showing an example of a hardware configuration of a console.

A description of an example of a hardware configuration of the console 50 will be made with reference to FIG. 7. As shown in FIG. 7, the console 50 includes a CPU 51, a non-volatile storage unit 52, and a memory 53 as a transitory storage region. In addition, the console 50 includes a display 54, such as a liquid crystal display, an operation unit 55, such as a touch panel, a keyboard, and a mouse, and an I/F unit 56. The I/F unit 56 performs wired or wireless communication with the imaging apparatus 10, the RIS 6, and other external apparatuses. The CPU 51, the storage unit 52, the memory 53, the display 54, the operation unit 55, and the OF unit 56 are connected to each other via a bus 58, such as a system bus and a control bus, so that various types of information can be exchanged.

The storage unit 52 is realized by, for example, a storage medium, such as an HDD, an SSD, and a flash memory. A control program 57 in the console 50 is stored in the storage unit 52. The CPU 51 reads out the control program 57 from the storage unit 52 to deploy the control program 57 into the memory 53, and executes the deployed control program 57. As the console 50, for example, a personal computer, a server computer, a smartphone, a tablet terminal, a wearable terminal, or the like can be applied as appropriate.

In addition, the storage unit 52 stores the image data of the radiation image and the ultrasound image acquired by the imaging apparatus 10, various types of other information, and the like. The image data of the radiation image and the ultrasound image may be stored in association with at least one of the imaging order or the imaging information. The imaging information may be, for example, at least one of examinee information and an imaging item that are included in the imaging order, photographer information indicating a photographer (for example, the user, such as the doctor or the technician) who performs the imaging, or date and time information indicating date and time when the imaging is performed.

Figure 8:
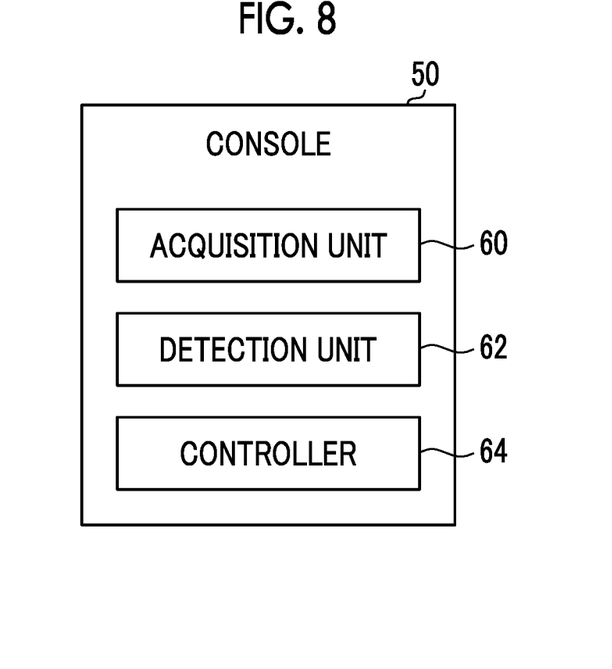
FIG. 8 is a block diagram showing an example of a functional configuration of the console.

A description of an example of a functional configuration of the console 50 will be made with reference to FIG. 8. As shown in FIG. 8, the console 50 includes an acquisition unit 60, a detection unit 62, and a controller 64. In a case in which the CPU 51 executes the control program 57, the CPU 51 functions as the acquisition unit 60, the detection unit 62, and the controller 64.

The acquisition unit 60 acquires the radiation image captured by irradiating the breast put into the compressed state by the compression member 40 with the radiation R, from the imaging apparatus 10. Specifically, the acquisition unit 60 may acquire the radiation image stored in the storage unit 22 of the imaging apparatus 10 via the I/F unit 56, may acquire the radiation image stored in the storage unit 52, or may acquire the radiation image stored in the external apparatus.

Figure 9:
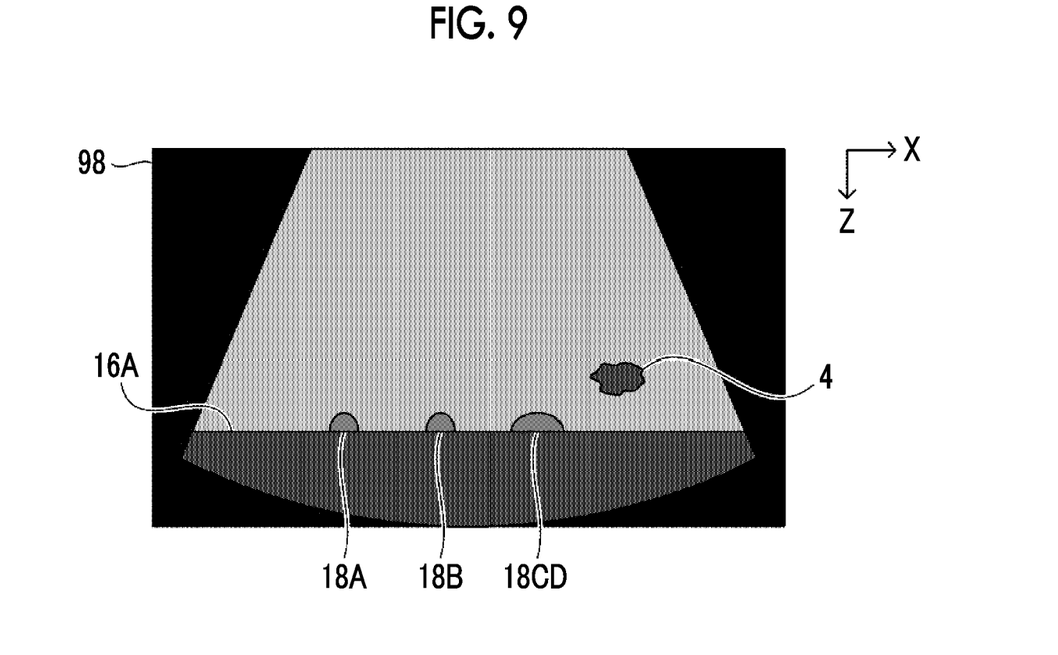
FIG. 9 is a view showing an example of an ultrasound image.

In addition, the acquisition unit 60 acquires the ultrasound image obtained by performing ultrasound imaging on the breast put into the compressed state by the compression member 40 with the ultrasound probe 30, from the imaging apparatus 10. FIG. 9 shows an example of an ultrasound image 98. As shown in FIGS. 5 and 6, the ultrasound image 98 of FIG. 9 is an image obtained by performing the ultrasound imaging on the breast disposed on the imaging surface 16A having the four markers 18A to 18D. However, the markers 18C and 18D disposed on the imaging surface 16A at the relatively close interval d3 are an integrated marker 18CD on the ultrasound image 98. The ultrasound image 98 includes a region of interest 4.

The detection unit 62 detects the marker 18 from the ultrasound image 98 acquired by the acquisition unit 60. For example, in FIG. 9, the detection unit 62 detects a plurality of markers 18A, 18B, and 18CD from the ultrasound image 98. In this case, the detection unit 62 determines that the two markers 18A and 18B among the four markers 18A to 18D can be appropriately detected, but the two markers 18C and 18D cannot be appropriately detected. It should be noted that, for example, in a case in which the number of detected markers is different from a predetermined number (four in the example of FIG. 9), the detection unit 62 may determine that the markers cannot be appropriately detected. In addition, for example, the detection unit 62 may measure the size of each of the detected markers 18A, 18B, and 18CD, and may determine that some markers are integrated and cannot be appropriately detected in a case in which there is the marker having the size equal to or larger than a predetermined threshold value.

For example, in a case in which the breast is large and thick or has a high-density mammary gland (dense breast), there is a possibility that no marker can be detected. Also in this case, the detection unit 62 determines that the marker 18 cannot be appropriately detected from the ultrasound image 98.

The controller 64 performs control of giving a warning in a case in which the detection unit 62 cannot detect the marker from the ultrasound image 98. For example, the controller 64 may perform control of displaying a warning sentence on the display 54, or may give notification by voice or the like. The controller 64 may perform control of displaying the radiation image and the ultrasound image acquired by the acquisition unit 60 on the display 54 in association with each other.

Figure 10:
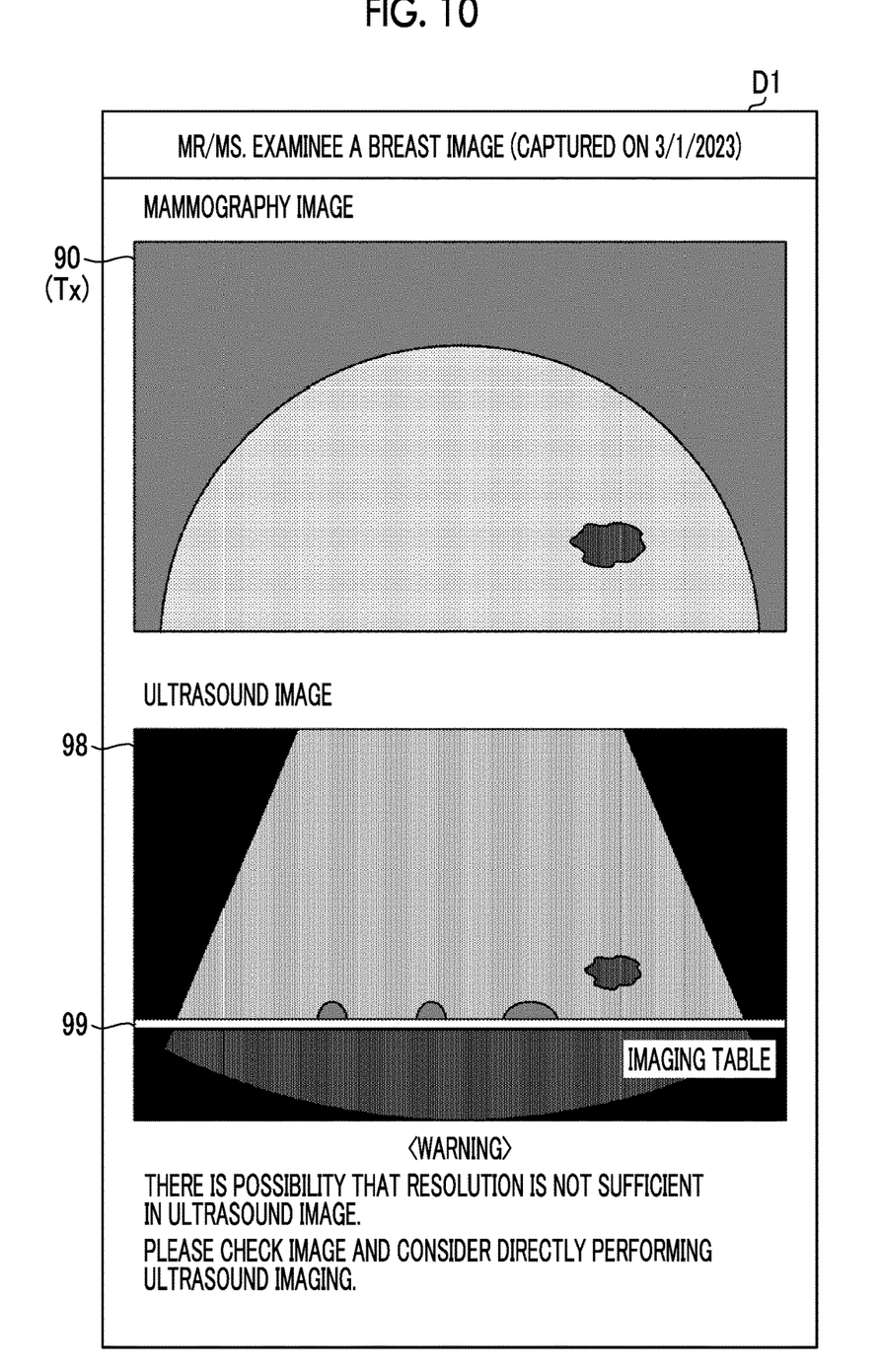
FIG. 10 is a view showing an example of a screen displayed on a display.

FIG. 10 shows an example of a screen D1 displayed on the display 54 by the controller 64. On the screen D1, a mammography image (radiation image) 90 and the ultrasound image 98 are displayed in association with each other. In the ultrasound image 98, the position of the imaging surface 16A specified from the markers 18A, 18B, and 18CD detected by the detection unit 62 is highlighted by a highlight 99. Since the detection unit 62 determines that the two markers 18C and 18D cannot be appropriately detected, a warning sentence indicating that the resolution is not sufficient is displayed.

The controller 64 may store the radiation image and the ultrasound image acquired by the acquisition unit 60 in the storage unit 52 of the console 50, the storage unit 22 of the imaging apparatus 10, an external storage device, or the like, in association with each other.

MODIFICATION EXAMPLE

The form is described in which a warning is given depending on whether or not the marker 18 can be detected from the ultrasound image, but the present disclosure is not limited to this. For example, even in a case in which the marker 18 cannot be detected, in a case in which the region of interest suspected to be abnormal is in a relatively shallow region near the compression member 40, a warning may not be necessary. Then, the console 50 may change whether or not to give a warning in accordance with the depth position of the region of interest, in addition to the detection result of the marker 18. Hereinafter, a description of a specific example of such a case will be made.

Figure 11:
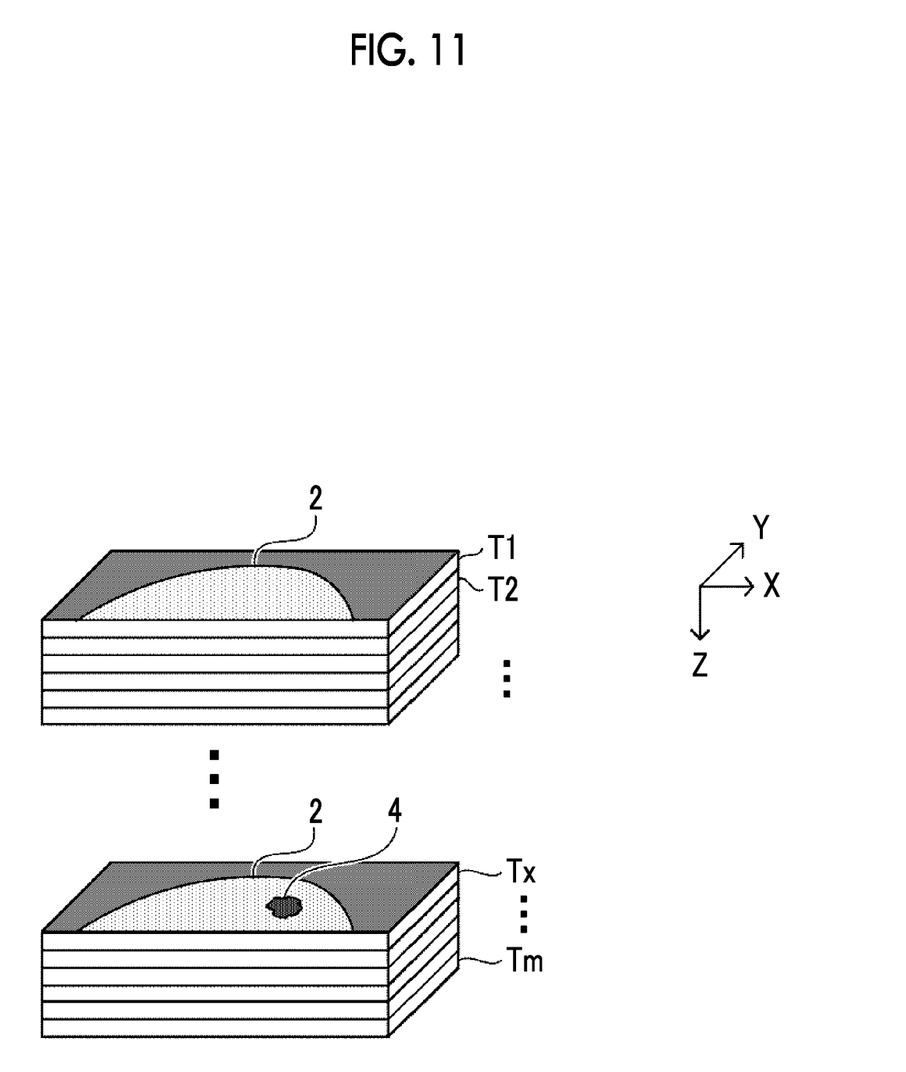
FIG. 11 is a view showing an example of a tomographic image.

The acquisition unit 60 acquires a tomographic image on each of a plurality of tomographic planes of the breast put into the compressed state by the compression member 40, from the imaging apparatus 10. FIG. 11 shows an example of a plurality of tomographic images T1 to Tm indicating any tomographic planes of the breast 2, respectively. These tomographic images T1 to Tm are obtained by, for example, the tomosynthesis imaging. In the example of FIG. 11, a certain tomographic image Tx includes the region of interest 4 suspected to be abnormal in the breast 2. The tomographic image T1 in FIG. 11 is a tomographic image on the contact surface between the compression member 40 and the breast 2.

The detection unit 62 specifies, for the region of interest 4 included in the breast 2, the depth position in the compression direction from the contact surface between the compression member 40 and the breast 2 based on the plurality of tomographic images T1 to Tm acquired by the acquisition unit 60. In the example of FIG. 11, the detection unit 62 derives a distance from the tomographic image T1 to the tomographic image Tx including the region of interest 4 in accordance with a slice thickness or the like, and specifies the derived distance as the depth position.

It should be noted that, as the method of specifying the position of the region of interest 4, for example, a method using a known computer aided detection/diagnosis (CAD) technique can be applied as appropriate. As the method of specifying the region of interest using the CAD technique, for example, a method using a learning model, such as a convolutional neural network (CNN), may be applied. For example, the detection unit 62 may specify the position of the region of interest in each of the tomographic images T1 to Tm by using a learning model trained to receive each of the tomographic images T1 to Tm as an input and then extract and output the region of interest included in each of the tomographic images T1 to Tm. In addition, for example, the detection unit 62 may specify the region designated by the user via the operation unit 55 as the region of interest.

The controller 64 performs the control of giving a warning in a case in which the depth position of the region of interest 4 detected by the detection unit 62 is equal to or greater than the predetermined threshold value and the marker 18 cannot be detected from the ultrasound image by the detection unit 62. As the threshold value, for example, the depth position or the like known in advance that a sufficient resolution is ensured can be set as appropriate regardless of individual differences in the breast.

Figure 12:
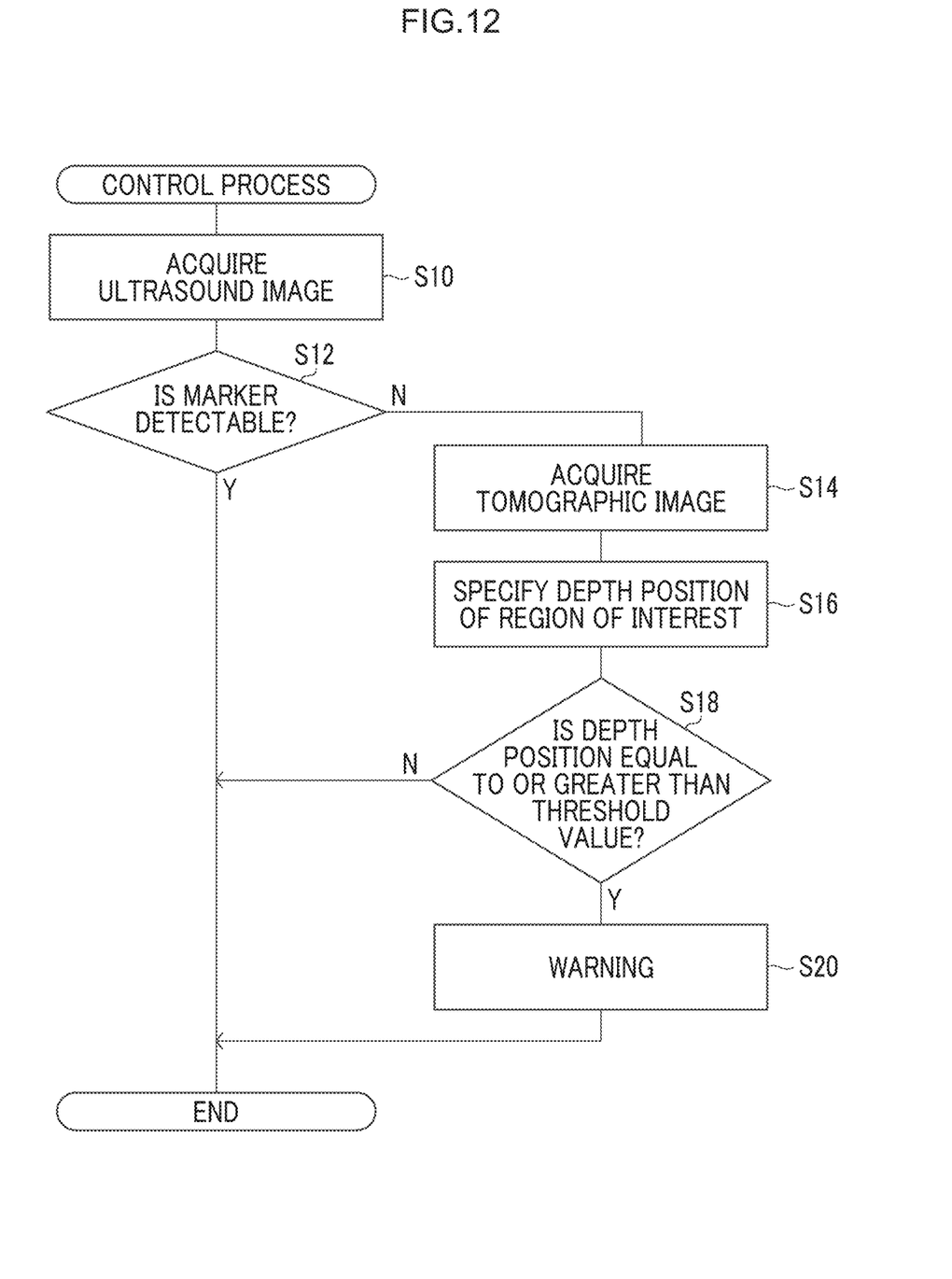
FIG. 12 is a flowchart showing an example of a control process.

Next, a description of an action of the console 50 according to the present embodiment will be made with reference to FIG. 12. In the console 50, the CPU 51 executes the control program 57 to execute a control process shown in FIG. 12. The control process is executed, for example, in a case in which the user gives an instruction to start the execution via the operation unit 55.

In step S10, the acquisition unit 60 acquires the ultrasound image captured by the imaging apparatus 10. In step S12, the detection unit 62 attempts to detect the marker 18 from the ultrasound image acquired in step S10. In a case in which the marker 18 can be detected in step S12, the present control process is terminated.

On the other hand, in a case in which the marker 18 cannot be detected in step S12 (in a case in which there are the plurality of markers 18, even a part of the markers 18 cannot be detected), the process proceeds to step S14. In step S14, the acquisition unit 60 acquires the tomographic image on each of the plurality of tomographic planes of the breast put into the compressed state by the compression member 40, from the imaging apparatus 10. In step S16, the detection unit 62 specifies, for the region of interest included in the breast, the depth position in the compression direction from the contact surface between the compression member 40 and the breast based on the plurality of tomographic images T1 to Tm acquired in step S14.

In step S18, the controller 64 determines whether or not the depth position of the region of interest specified in step S16 is equal to or greater than the predetermined threshold value. In a case in which the depth position of the region of interest is smaller than the predetermined threshold value in step S18, the marker 18 cannot be detected, but the region of interest is in a relatively shallow region close to the compression member 40. Therefore, a warning is not necessary, and the present control process is terminated.

On the other hand, in a case in which the depth position of the region of interest is equal to or greater than the predetermined threshold value in step S18, the process proceeds to step S20. In step S20, the controller 64 performs the control of giving a warning by determining that the depth position of the region of interest is equal to or greater than the predetermined threshold value and the marker 18 cannot be detected from the ultrasound image. In a case in which step S20 is completed, the present control process is terminated.

As described above, the imaging apparatus 10 according to the aspect of the present disclosure comprises the imaging table 16 having the imaging surface 16A on which at least one marker 18 is disposed, the compression member 40 for putting the breast 2 disposed on the imaging surface 16A into the compressed state, and the ultrasound probe 30 that obtains the ultrasound image of the breast 2 put into the compressed state by the compression member 40.

That is, with the imaging apparatus 10 according to the present embodiment, by checking whether or not the marker 18 can be detected from the captured ultrasound image, it is possible to check whether or not the ultrasound image with sufficient accuracy can be captured particularly for the portion (imaging table 16 side) away from the ultrasound probe 30 in the breast 2 that is the examination target. Therefore, it is possible to support the capturing of the ultrasound image with the accuracy that enables to read the marker provided on the imaging table.

It should be noted that, in the embodiment described above, the form is described in which the console 50 is an example of a control apparatus according to the present disclosure, but an apparatus other than the console 50 may have the function of the control apparatus according to the present disclosure. In other words, an apparatus other than the console 50, such as the imaging apparatus 10 and the external apparatus, may have a part or all of the functions of the acquisition unit 60, the detection unit 62, and the controller 64.

In the embodiment described above, for example, as hardware structures of processing units that execute various types of processes, such as the controller 20, the acquisition unit 60, the detection unit 62, and the controller 64, various processors shown below can be used. As described above, in addition to the CPU that is a general-purpose processor that executes software (program) to function as various processing units, the various processors include a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by using one of the various processors or may be configured by using a combination of two or more processors of the same type or different types (for example, a combination of a plurality of FPGAs or a combination of a CPU and an FPGA). Moreover, a plurality of processing units may be configured of one processor.

A first example of the configuration in which the plurality of processing units are configured by using one processor is a form in which one processor is configured by using a combination of one or more CPUs and the software and this processor functions as the plurality of processing units, as represented by computers, such as a client and a server. Second, as represented by a system on chip (SoC) or the like, there is a form in which the processor is used in which the functions of the entire system which includes the plurality of processing units are realized by a single integrated circuit (IC) chip. In this way, as the hardware structure, the various processing units are configured by using one or more of the various processors described above.

Further, the hardware structure of these various processors is, more specifically, an electric circuit (circuitry) in which circuit elements such as semiconductor elements are combined.

In addition, in the embodiment described above, the aspect is described in which the various programs in the imaging apparatus 10 are stored (installed) in the ROM included in the controller 20 in advance, and the control program 57 in the console 50 is stored in the storage unit 52 in advance, but the present disclosure is not limited to this. The various programs and the control program 57 in the imaging apparatus 10 may be provided in a form of being recorded in a recording medium, such as a compact disc read only memory (CD-ROM), a digital versatile disc read only memory (DVD-ROM), and a universal serial bus (USB) memory. In addition, a form may be adopted in which the various programs and the control program 57 in the imaging apparatus 10 are downloaded from an external apparatus via the network. Further, the technique of the present disclosure extends to a storage medium that non-transitorily stores a program in addition to the program.

In the technique of the present disclosure, the embodiment and the examples described above can be combined as appropriate. The above-described contents and the above-shown contents are detailed description for parts according to the technique of the present disclosure, and are merely examples of the technique of the present disclosure. For example, the above description related to the configuration, the function, the action, and the effect is the description related to the examples of the configuration, the function, the action, and the effect of the parts according to the technique of the present disclosure. As a result, it is needless to say that unnecessary parts may be deleted, new elements may be added, or replacements may be made with respect to the above-described contents and the above-shown contents within a range that does not deviate from the gist of the technique of the present disclosure.

What is claimed is:

1. An imaging system comprising:
   an imaging apparatus including:
      an imaging table having an imaging surface on which at least one marker is disposed;
      a compression member for putting a breast disposed on the imaging surface into a compressed state;
      an ultrasound probe configured to obtain an ultrasound image of the breast put into the compressed state by the compression member; and
   a control apparatus including at least one processor,
   wherein the at least one processor is configured to:
      acquire the ultrasound image of the breast obtained by the ultrasound probe;
      detect the at least one marker from the ultrasound image; and
      give a warning in a case in which the at least one marker is not detectable from the ultrasound image.

2. The imaging system according to claim 1, wherein the at least one marker is formed of a material having a different acoustic impedance from at least a region adjacent to the at least one marker on the imaging surface.

3. The imaging system according to claim 1, wherein the at least one marker is a portion formed in a recess shape or a protrusion shape with respect to the imaging surface.

4. The imaging system according to claim 1, wherein three or more markers having different intervals between adjacent markers are disposed on the imaging surface.

5. The imaging system according to claim 1, further comprising a radiation source that irradiates the breast put into the compressed state by the compression member with radiation,
   wherein the at least one marker is disposed on the imaging surface in a region other than an irradiation field of the radiation.

6. The imaging system according to claim 1, wherein the at least one processor is configured to:
   acquire a tomographic image on each of a plurality of tomographic planes of the breast put into the compressed state by the compression member;
   specify a depth position in a compression direction from a contact surface between the compression member and the breast for a region of interest included in the breast based on a plurality of the tomographic images; and
   give a warning in a case in which the depth position of the region of interest is equal to or greater than a predetermined threshold value and the at least one marker is not detectable from the ultrasound image.

7. A control method comprising:
   acquiring an ultrasound image of a breast that is disposed on an imaging surface, on which at least one marker is disposed, of an imaging table having the imaging surface, and is put into a compressed state by a compression member;
   detecting the at least one marker from the ultrasound image; and
   giving a warning in a case in which the at least one marker is not detectable from the ultrasound image.

8. A non-transitory computer-readable storage medium storing a control program for causing a computer to execute a process comprising:
   acquiring an ultrasound image of a breast that is disposed on an imaging surface, on which at least one marker is disposed, of an imaging table having the imaging surface, and is put into a compressed state by a compression member;
   detecting the at least one marker from the ultrasound image; and
   giving a warning in a case in which the at least one marker is not detectable from the ultrasound image.

* * * * *